United States Patent
Skolik (12)

(10) Patent No.: US 7,077,831 B2
(45) Date of Patent: Jul. 18, 2006

(54) OPHTHALMIC FLUID DISPENSER

(76) Inventor: Stephanie Skolik, 1300 12th St., Huntington, WV (US) 25701

( * ) Notice: Subject to any disclaimer, the term of this patent is extended or adjusted under 35 U.S.C. 154(b) by 229 days.

(21) Appl. No.: 10/733,951

(22) Filed: Dec. 11, 2003

(65) Prior Publication Data

US 2005/0131358 A1   Jun. 16, 2005

(51) Int. Cl.
*A61M 35/00* (2006.01)
*A61M 11/00* (2006.01)
(52) U.S. Cl. .................. 604/296; 604/298; 604/300; 128/200.14; 222/519
(58) Field of Classification Search ........ 604/294–302; 128/200.14, 200.17, 200.21, 200.23, 200.22; 222/21, 631, 367–369, 410, 519
See application file for complete search history.

(56) References Cited

U.S. PATENT DOCUMENTS

| | | | | | |
|---|---|---|---|---|---|
| 3,261,355 | A | * | 7/1966 | Burbig .................. | 604/296 |
| 3,934,585 | A | * | 1/1976 | Maurice ................. | 604/298 |
| 4,002,168 | A | | 1/1977 | Petterson | |
| 4,667,854 | A | * | 5/1987 | McDermott et al. ........ | 222/101 |
| 4,784,652 | A | * | 11/1988 | Wikstrom ............... | 604/295 |
| 5,133,701 | A | * | 7/1992 | Han ..................... | 604/289 |
| 5,152,435 | A | * | 10/1992 | Stand et al. ............. | 222/309 |
| 5,201,726 | A | * | 4/1993 | Kirkham ................ | 604/294 |
| 5,346,132 | A | * | 9/1994 | Hahn et al. .............. | 239/71 |
| 5,578,019 | A | * | 11/1996 | Feldman ................ | 604/295 |
| 5,607,410 | A | * | 3/1997 | Branch ................. | 604/302 |
| 5,685,869 | A | * | 11/1997 | Py ...................... | 604/294 |
| 5,902,292 | A | * | 5/1999 | Feldman ................ | 604/295 |
| 6,398,766 | B1 | * | 6/2002 | Branch ................. | 604/302 |
| 6,413,246 | B1 | * | 7/2002 | Harrold ................ | 604/298 |
| 6,419,663 | B1 | * | 7/2002 | Harrold ................ | 604/298 |
| 6,423,040 | B1 | * | 7/2002 | Benktzon et al. ......... | 604/300 |
| 6,506,183 | B1 | * | 1/2003 | Cogger ................. | 604/298 |
| 6,524,287 | B1 | * | 2/2003 | Cogger ................. | 604/298 |
| RE38,077 | E | * | 4/2003 | Cohen et al. ............ | 239/333 |
| 6,569,131 | B1 | * | 5/2003 | Michael et al. .......... | 604/295 |
| 6,758,837 | B1 | * | 7/2004 | Peclat et al. ............ | 604/295 |

FOREIGN PATENT DOCUMENTS

WO    WO 98/55059    12/1998

* cited by examiner

*Primary Examiner*—Tatyana Zalukaeva
*Assistant Examiner*—Michael G. Bogart
(74) *Attorney, Agent, or Firm*—Pandiscio & Pandiscio (57) ABSTRACT

An eye fluid applicator is adapted for connection to the mouth of a bottle containing an ophthalmic liquid and comprises means for dispensing ophthalmic liquid from the bottle in metered amounts and in a manner which avoids contacting the eye with the applicator. The applicator includes a metering member that has a metering cavity for holding a small amount of liquid and which is movable between a first position in which the metering cavity is disposed to receive liquid from the container and a second position in which it allows the liquid to spill out of the cavity into a holding chamber, and manually operable pneumatic means for removing liquid from the holding chamber and expelling it through a discharge orifice in the form of a narrow spray.

25 Claims, 11 Drawing Sheets

OPHTHALMIC FLUID DISPENSER

FIELD OF THE INVENTION

The invention pertains to delivery of ophthalmic fluids to the eye and more particularly to a device for dispensing ophthalmic fluid in small controlled doses.

BACKGROUND OF THE INVENTION

Ophthalmic products are available for treatment of various conditions. For example, the treatment of glaucoma requires frequent daily administrations of certain ophthalmic compositions having the desired pressure-relieving action. Ophthalmic fluids also are used to relieve eye strain and irritation caused by smog, allergens such as pollen and dust, smoking, and swimming, etc. In the application of certain medical preparations, it is necessary that the fluid be delivered in a fairly well-defined volume since an excessive dosage may result in improper physiological effects. Another requirement is that the need to properly target the dose of ophthalmic medication. A contributing factor in requiring the delivery of a specified dose is the matter of cost in the case of expensive medications. Many ophthalmic fluids may be self-administered by the user. Accordingly in the case of self-treatment, a further consideration is the need to achieve delivery to the targeted eye without the patient having to assume a strained body, head or hand position, since such a strained posture may result in forced errors. Another important factor to consider in facilitating patient self-treatment and operator-assisted treatment is that ophthalmic medications are commonly sold in small bottles which are not designed to function as controlled dosage applicators. Therefore there is a need for dispenser/applicator device that is adapted to accept conventional ophthalmic product bottles, with the containers being easy to install and replace, and with the device filling control being unaffected by the size of the ophthalmic product container. An important consideration in using an applicator device to administer ophthalmic products to the eye is the need to maintain a sterile condition in the applicator.

A number of different applicator devices are known for dispensing an ophthalmic product to the eye of a patient. Such known devices suffer from various limitations. Certain devices for small volumes are based either on drop or on spray delivery principals. Drop applicators rely on impact by gravity, but common designs give little control over the administration of ophthalmic products. Certain devices are difficult to operate except with proper orientation of the device. Spray applicators rely on a shower. While prior spray applicators tend to be independent of applicator orientation and give a distributed spray, they are limited in controlling the amount that is dispensed. In some devices contamination can result from contaminants being drawn into the applicator after some product has been dispensed. Accordingly, there remains a need for a fluid eye applicator better meeting the demands for dispensing ophthalmic medications in controller amounts.

OBJECT AND SUMMARY OF THE INVENTION

A main object of the invention is to provide a dispenser for applying an ophthalmic product to the eye which permits patient self-treatment without requiring the patient to have exceptional mechanical dexterity in order to achieve the desired dosage or to deliver it to the targeted eye.

Another object of the invention is to provide an eye fluid applicator that is designed to dispense a predetermined dose of an ophthalmic product in the form of a narrow spray.

Still another object is to provide an eye fluid applicator which is adapted for connection to a bottle of an ophthalmic solution and to dispense that solution from the bottle in limited amounts and in a manner which avoids contacting the eye, thereby eliminating the possibility of contamination of the contents of the device in the case where an eye is infected or contagious.

A further object of the invention is to provide a dispenser for ophthalmic medications which permits self-treatment by the patient and does not require the patient to assume a strained body position in order to apply the ophthalmic medication.

A more specific object is to provide a device of the character described which may be made of a plastic material, has a relatively low cost, and is designed to reliably dispense a limited quantity of ophthalmic solution each time it is operated.

These and other objects are achieved by a device which essentially comprises a body that is adapted to be attached to the mouth of a bottle containing a quantity of an ophthalmic fluid, means for receiving and holding a limited quantity of ophthalmic fluid from the bottle, and means for dispensing that limited quantity of ophthalmic fluid to the eye of a patient in the form of a spray. The amount of fluid that is dispensed is metered by means of a member that has a cavity which is movable from a first position in which it is disposed to receive fluid from the container and a second position in which it allows the fluid to pass to a holding chamber, and the device further includes means for removing fluid from the holding chamber in the form of a spray, with the spray delivery being accomplished by means of an air stream injected into the holding chamber.

Other features and advantages of the invention are described in or rendered apparent by the following detailed description of a preferred embodiment of the invention, which is to be considered together with the accompanying drawings.

SPECIFIC DESCRIPTION OF THE PREFERRED EMBODIMENT

Referring to FIGS. 1–7, a dispenser device constituting a preferred embodiment of the present invention comprises a housing in the form of a body 2 having an axial cavity 4 with an enlarged outer end characterized by a screw thread 6 for use in attaching a bottle 8 (FIG. 12) containing an ophthalmic liquid (not shown). The inner end of cavity 4 is intersected by a diametrically-extending bore 12, resulting in the formation of a hole 13 (FIGS. 1 and 2) at the bottom cavity 4. The diameter of hole 13 is equal to or slightly greater than that of metering cavity 18 described hereinafter. Preferably, but not necessarily, the outer surface of body 2 is provided with an outwardly projecting circular boss 14 at each end of bore 12. The outer face of each boss is flat and acts as a bearing surface for the operating lever 86 described below.

Mounted within bore 12 is a metering member 16 in the form of a cylindrical shaft having a cavity 18 located intermediate its ends. Cavity 18 acts as a metering and transfer chamber, being sized to accommodate a predetermined volume of liquid. Preferably cavity 18 has a generally hemispherical shape, but it may have some other shape instead. By way of example but not limitation, cavity 18 may have a diameter of about 2 mm measured horizontally, i.e. in a plane extending parallel to the axis of metering member 16, and a depth of about 1 mm, thereby providing a volume of about 10 to 12 microliters (μl), depending on the slope of surface defining the cavity. Cavity 18 is located so that it can be moved by rotation of member 16 into alignment with hole 13.

Figure 1:
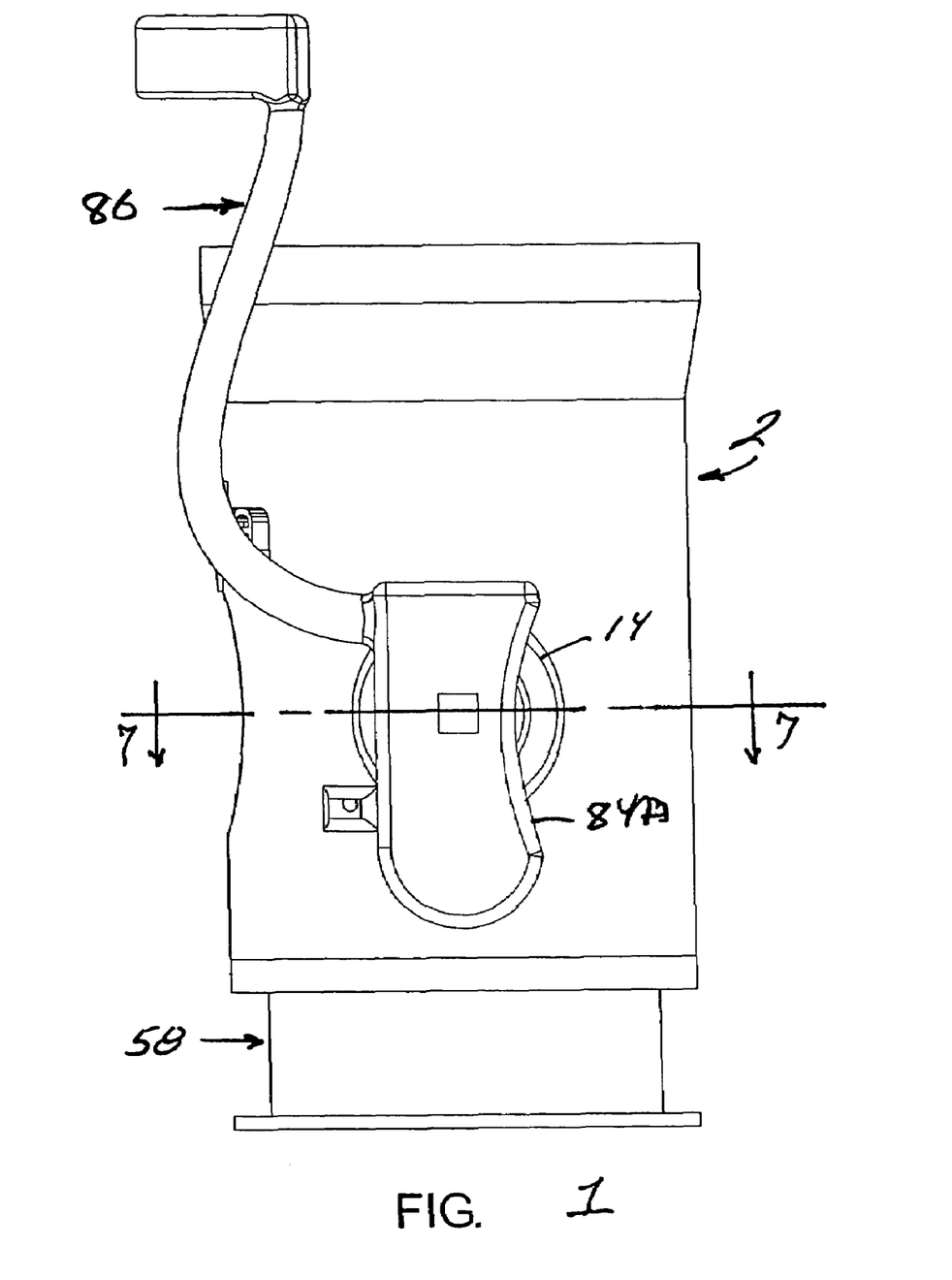
FIG. 1 is a side view in elevation of a device constituting a preferred embodiment of the invention.
Figure 2:
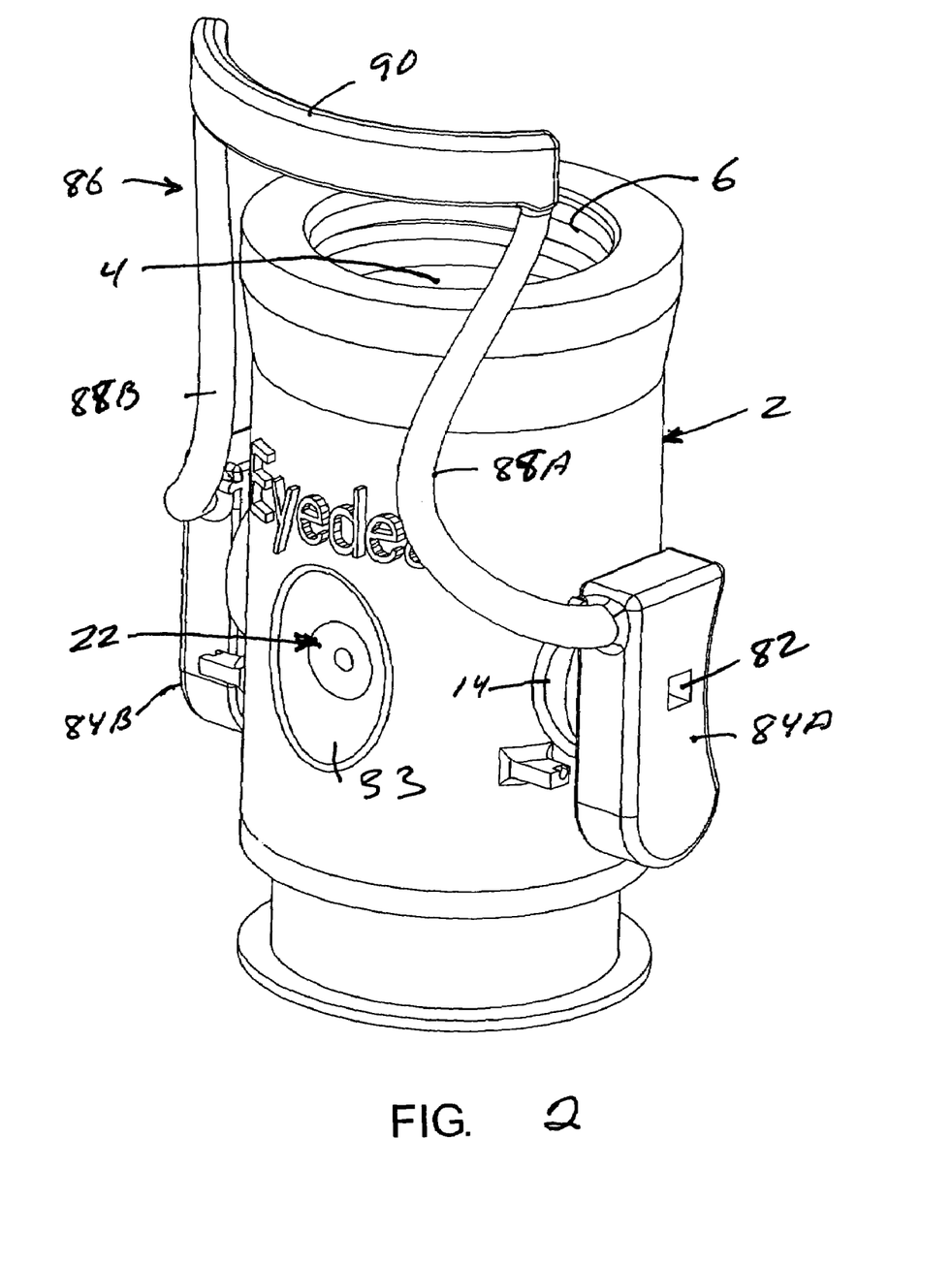
FIG. 2 is a perspective view in elevation of the same device.
Figure 3:
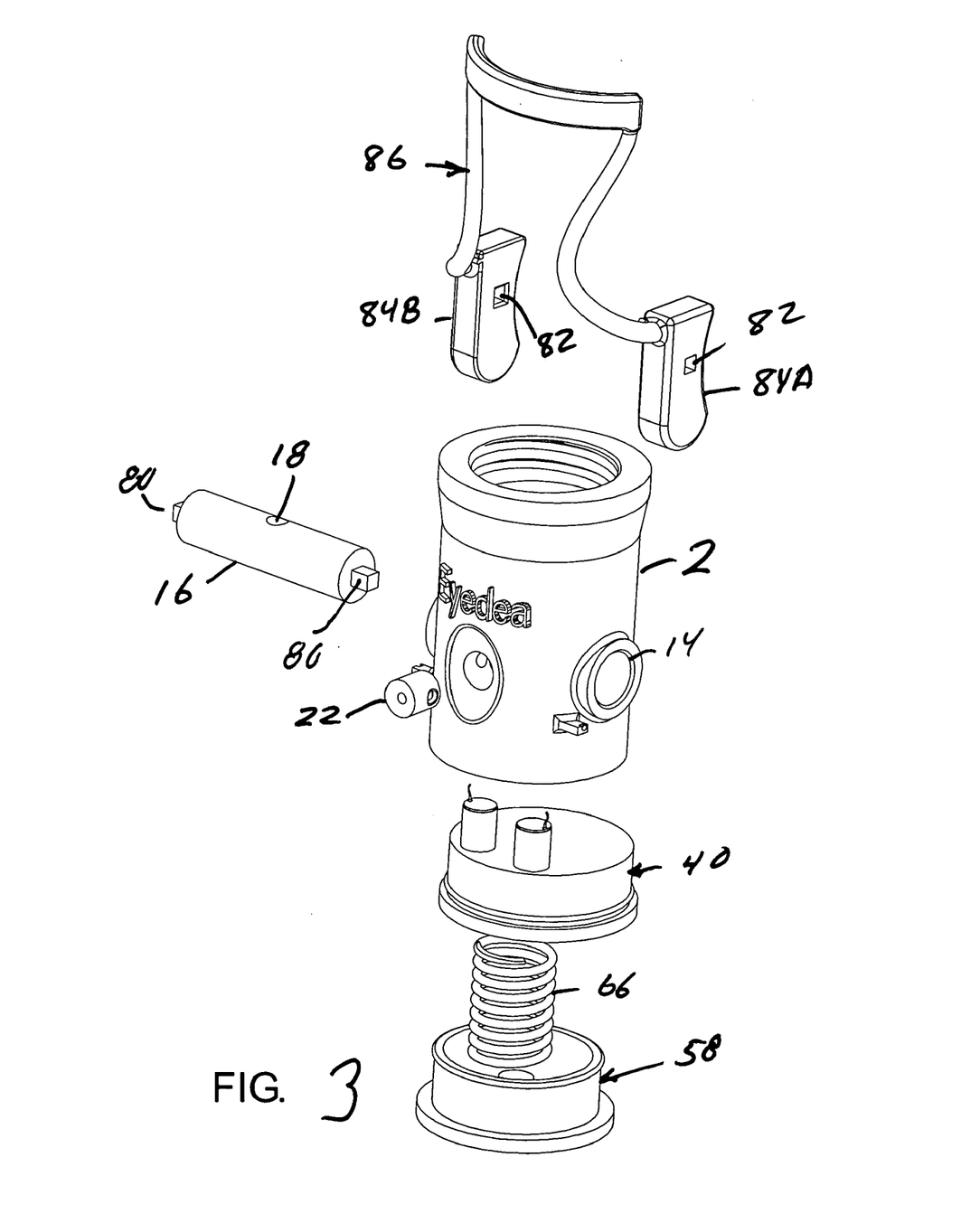
FIG. 3 is an exploded perspective view of the same device.
Figure 4:
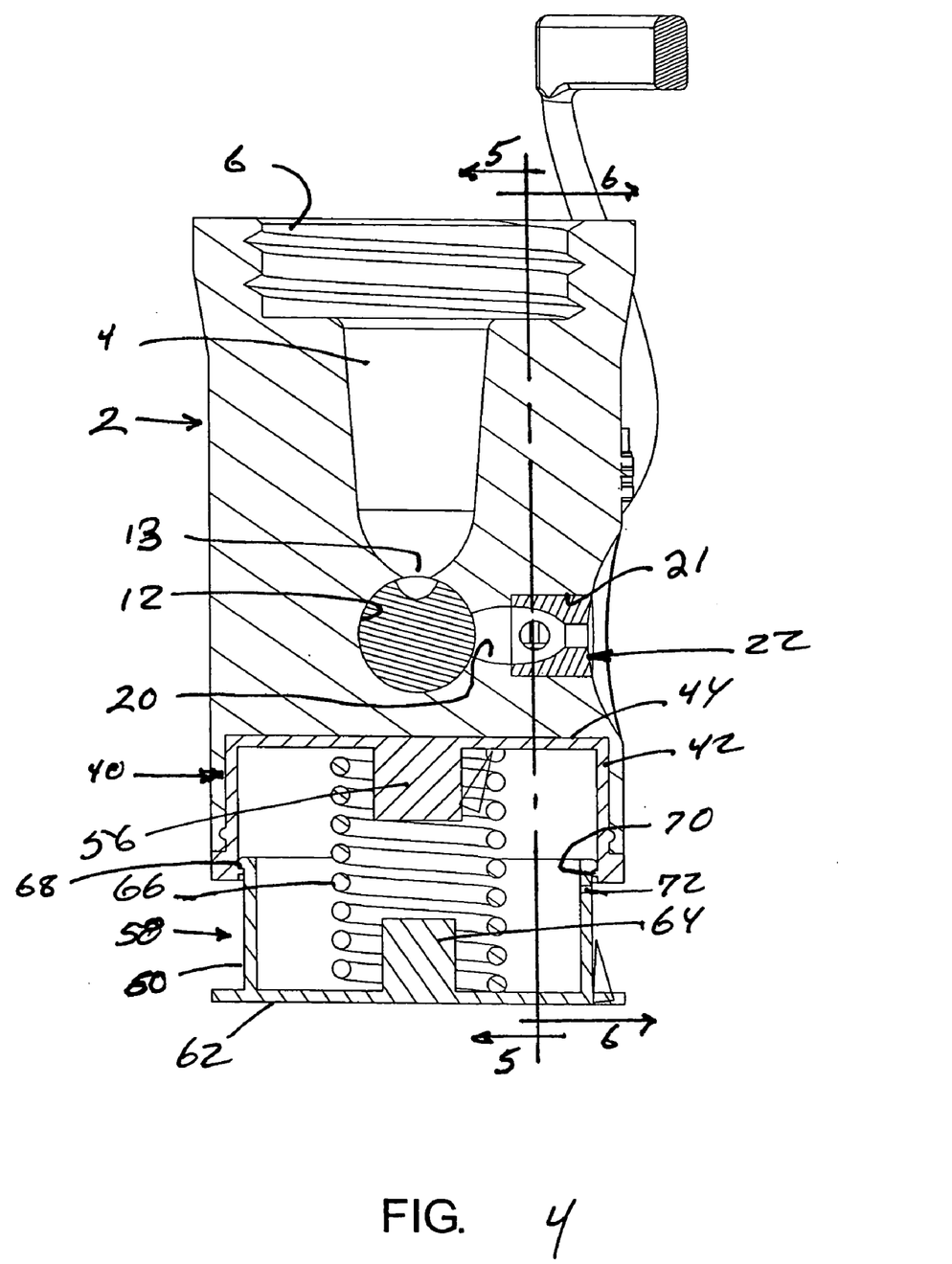
FIG. 4 is a longitudinal center line sectional view in elevation of the same device.
Figure 5:
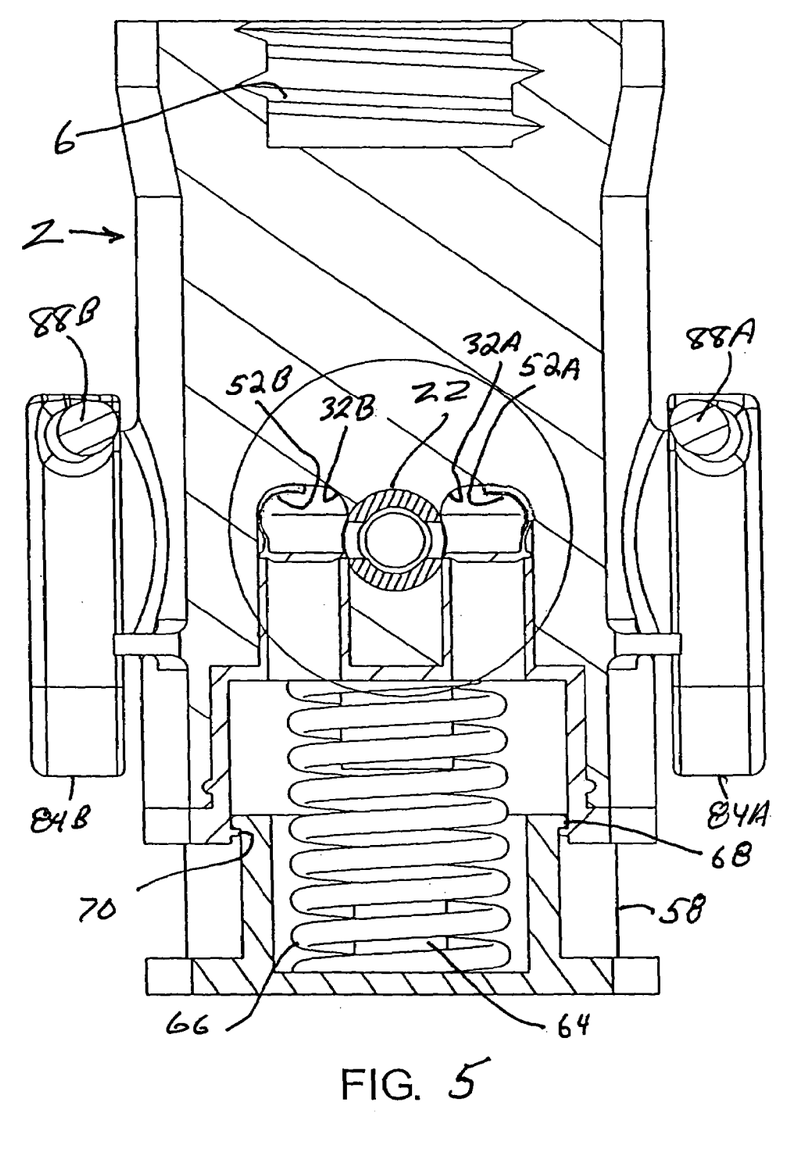
FIG. 5 is a longitudinal sectional view taken along line 5—5 of FIG. 4.
Figure 6:
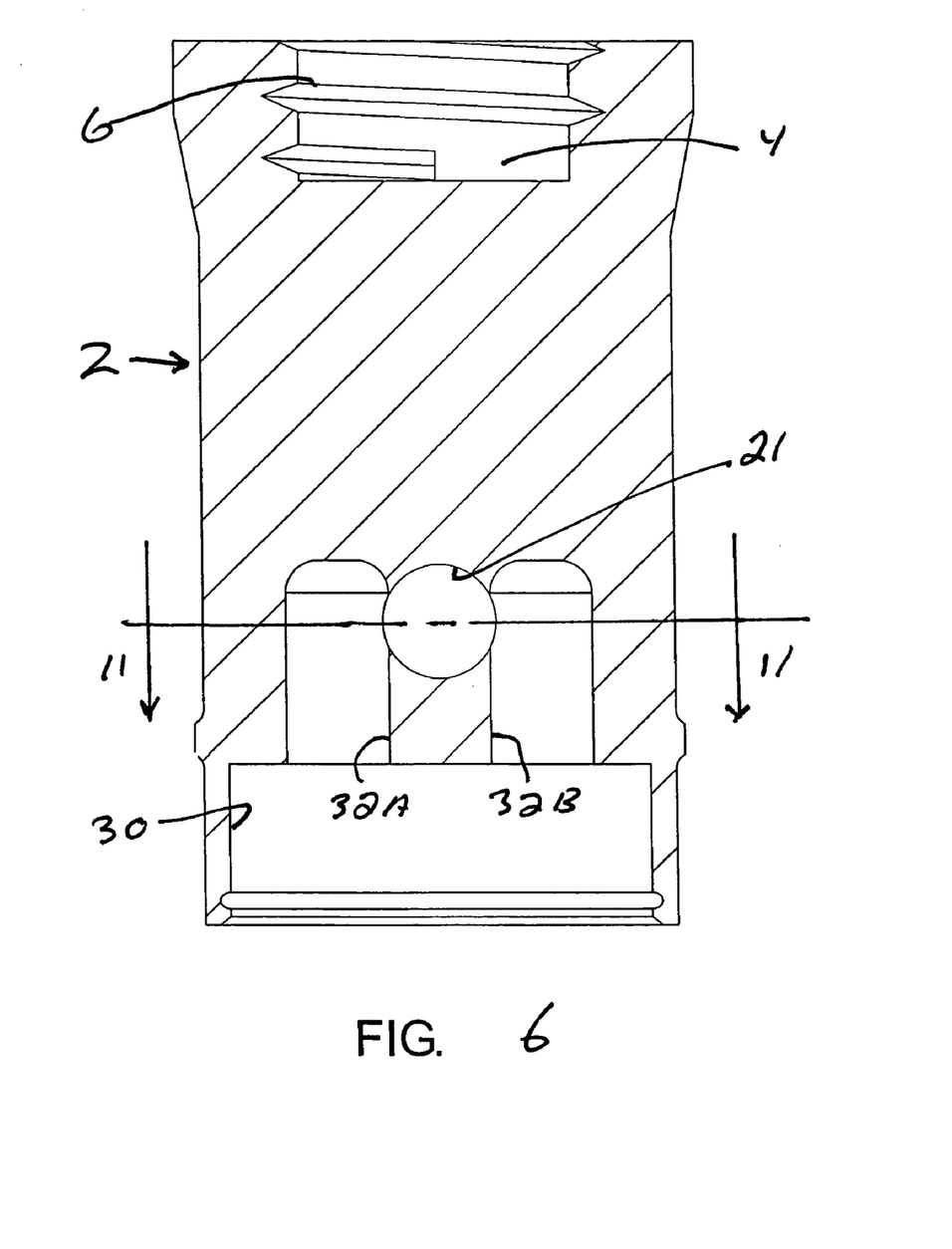
FIG. 6 is a longitudinal sectional view of the body of the same device, taken along the plane identified by line 6—6 in FIG. 4.
Figure 7:
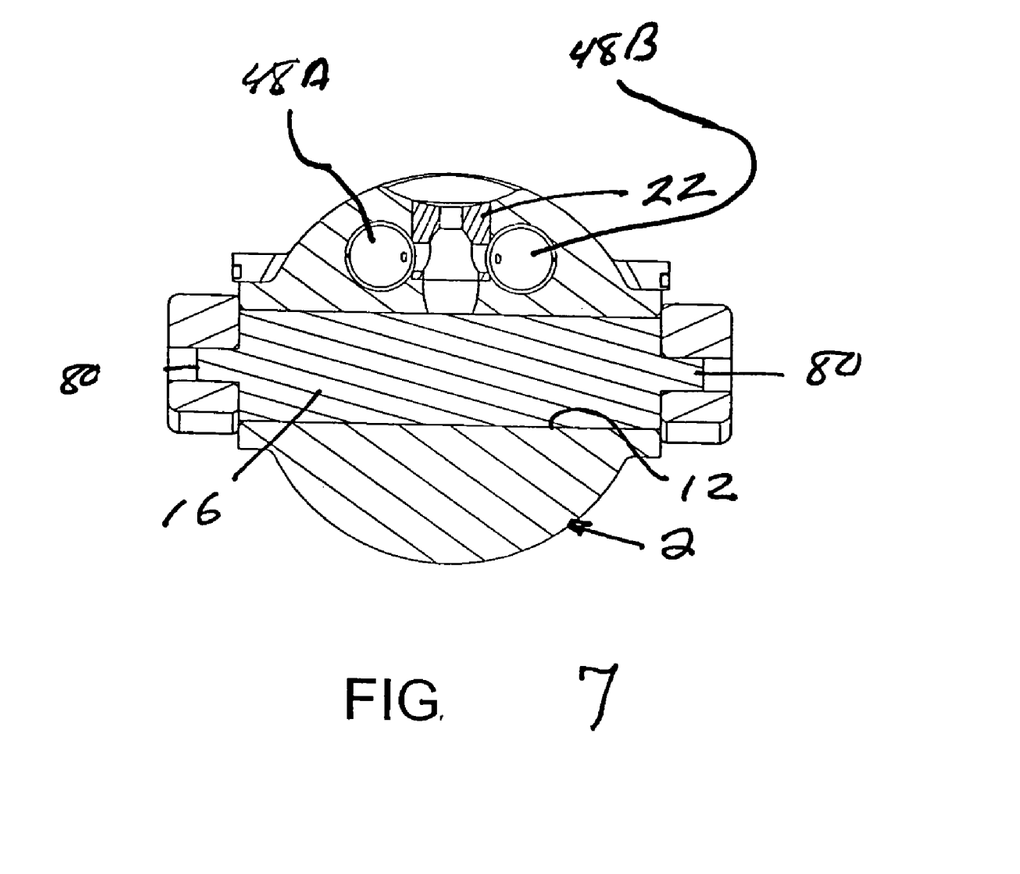
FIG. 7 is a cross-sectional view taken along line 7—7 of FIG. 1.

Referring to FIGS. 4–6, the lower end of body 2 is formed with a cylindrical cavity 30 and two blind holes 32A and 32B that form extensions of cavity 30. Cavity 30 is axially aligned with cavity 4. Blind holes 32A and 32B are located eccentric to the axis of housing 2.

Figure 8:
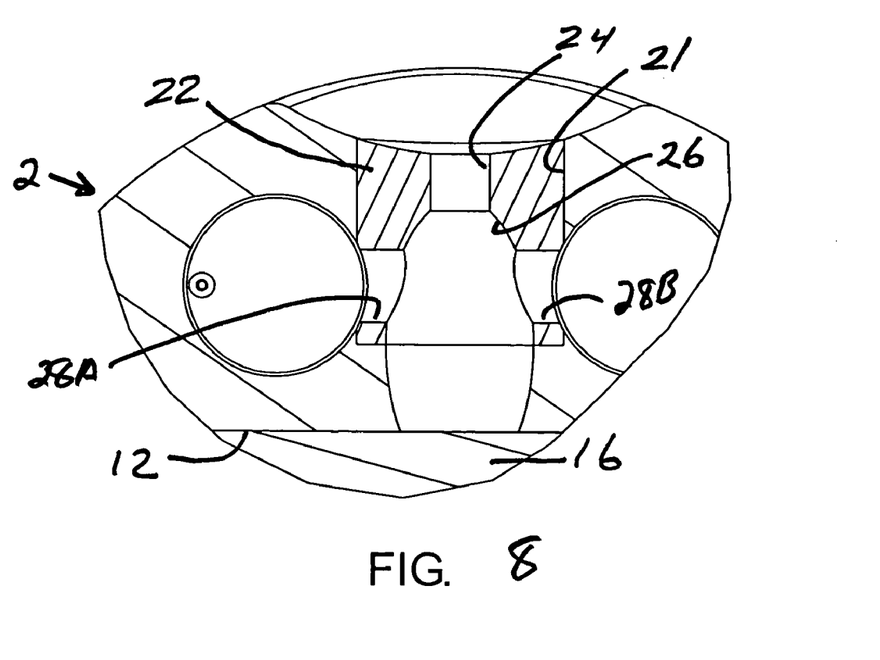
FIG. 8 is an enlargement of a portion of FIG. 7 illustrating details of the orifice insert and the metering member.
Figure 9:
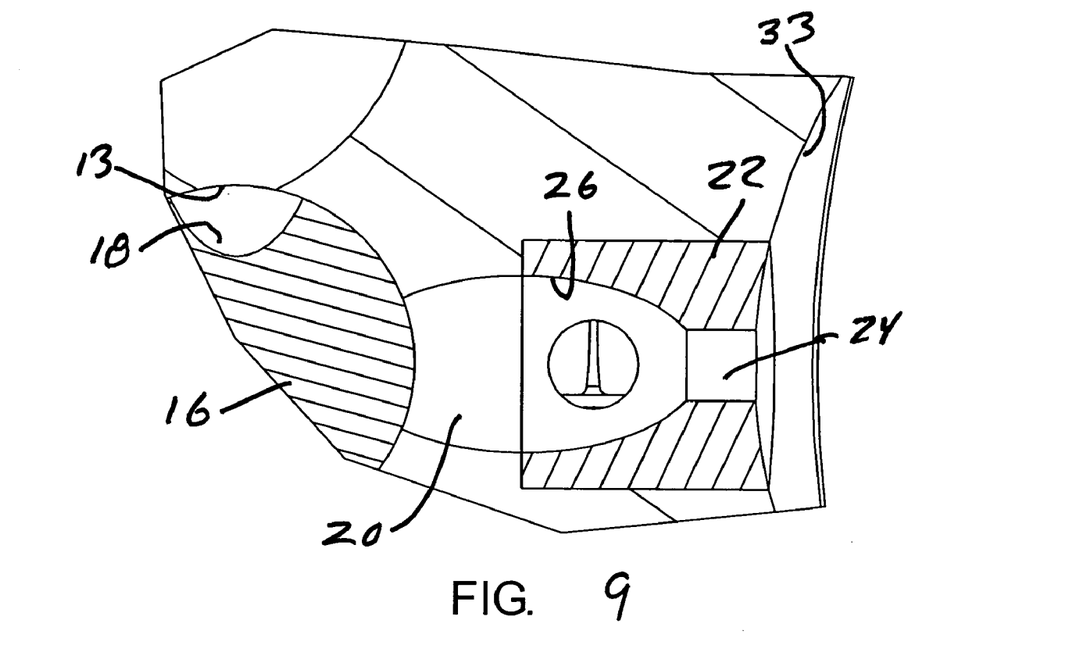
FIG. 9 is an enlargement of a portion of FIG. 4.
Figure 11:
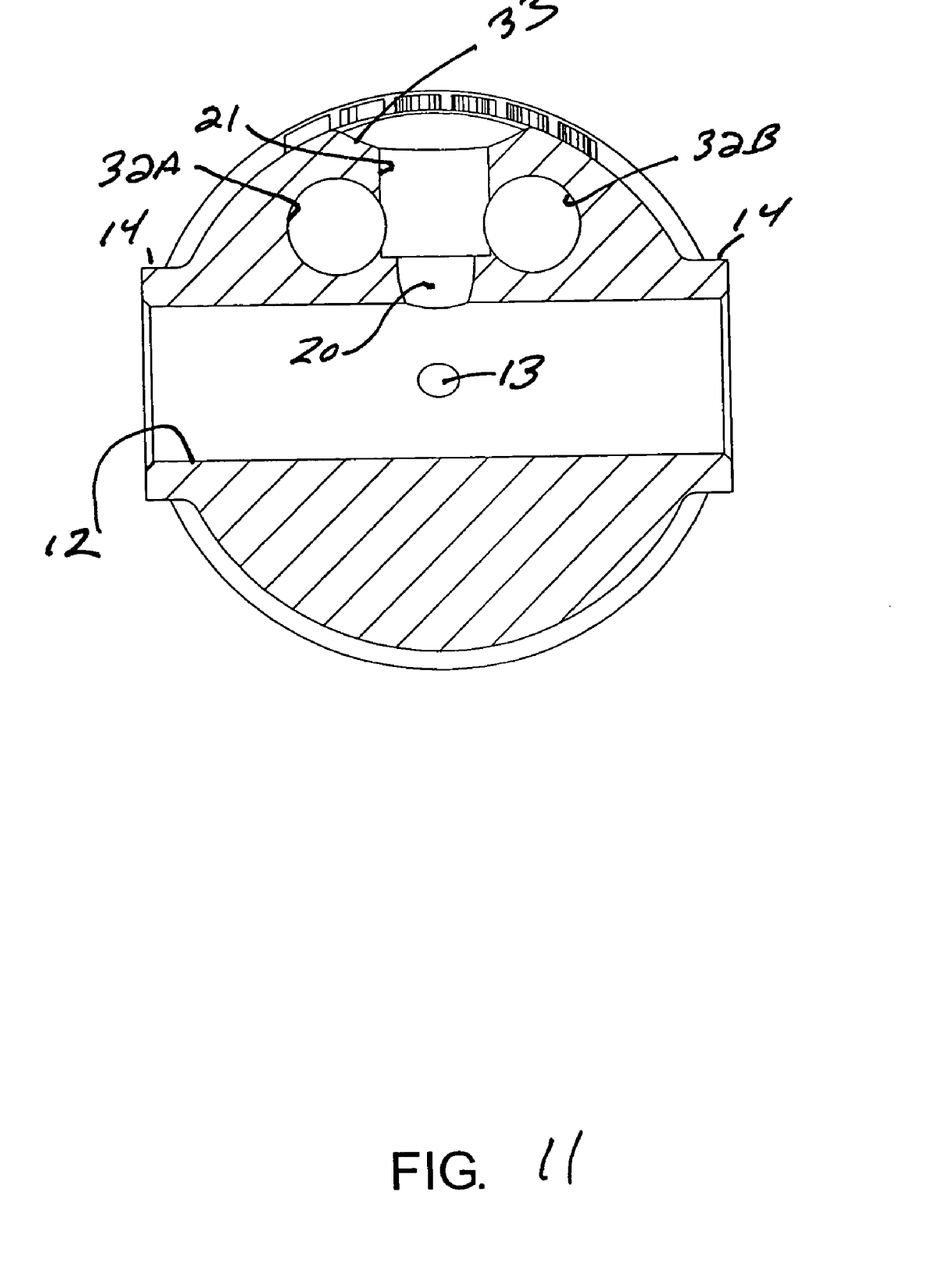
FIG. 11 is a cross-sectional view taken along lines 11—11 of FIG. 6.

Referring to FIGS. 4, 7–9 and 11, body 2 also is provided with a radial bore 20 that extends perpendicular to bore 12 and the axis of cavity 4. The inner portion of bore 20 may have a constant diameter, but preferably it is tapered down to a diameter closer to that of cavity 18 of metering member 16, as shown in FIG. 9. The outer portion of bore 20 has a counterbore 21 to accommodate an orifice insert 22. Orifice insert 22 is formed with a small diameter orifice 24 at its outer end, and an enlarged flared counterbore 26 at its inner end that preferably forms a smooth continuation of the inner portion of bore 20. By way of example but not limitation, orifice 24 may have a diameter of about 0.6 to about 0.7 mm. Bore 20 and the center axis of orifice insert 22 extend along a line that intersects at a right angle the portion of metering member 16 that has the cavity 18. Orifice insert 22 also has two side openings 28A and 28B (FIG. 8) that are aligned with each other parallel to bore 12. As illustrated in FIGS. 6, 8 and 11, the counterbore 21 intersects blind holes 32A and 32B a selected distance below their inner ends. As seen best in FIG. 8, the side openings 28A and 28B in orifice insert 22 are located so that they are aligned in a plane that includes the center axis of blind holes 32A and 32B, with the result that air can flow via openings 28A and 28B between the upper ends of blind holes 32A and 32B and the counterbore 26 of insert 22.

Figure 10A:
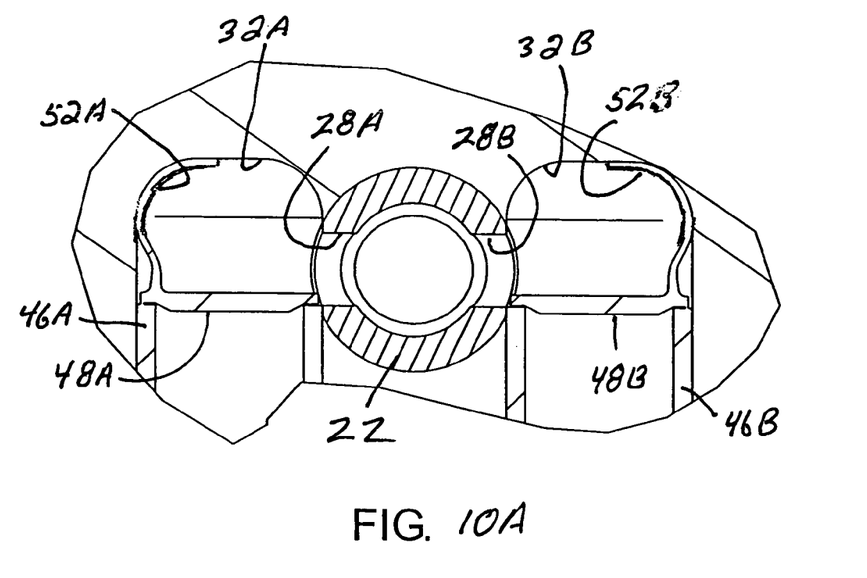
FIGS. 10A and 10B are enlargements of a portion of FIG. 5.
Figure 10B:
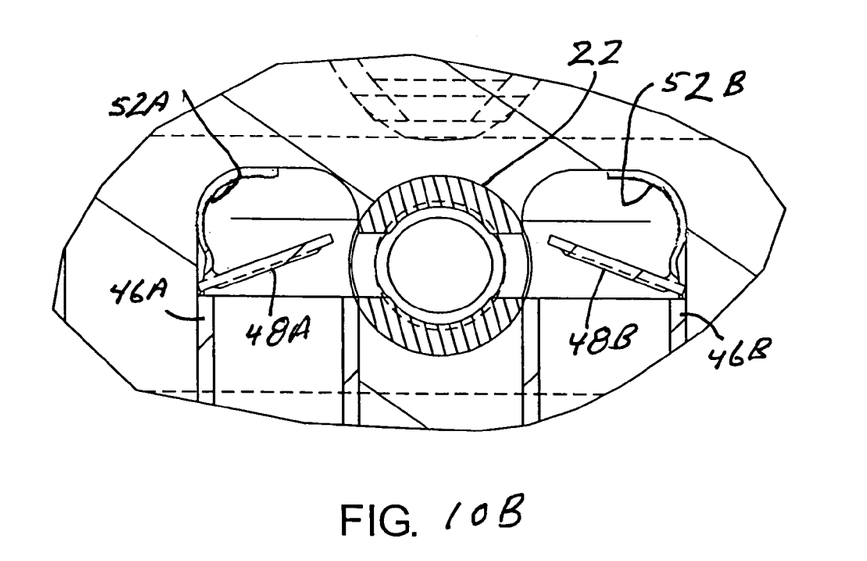

Referring to FIGS. 4, 5 and 9, mounted in the opening 30 is a cup-shaped member 40 having a side wall 42 and an end wall 44. The latter has two openings that are provided with cylindrical extensions 46A and 46B that extend into and make a close fit with blind holes 32A and 32B. As seen best in FIGS. 10A and 10B, these tubular extensions terminate even or slightly below the lowermost portion of side openings 28A and 28B of orifice insert 22, so that air can pass between tubular extensions 46A and 46B and openings 28A and 28b respectively. The upper ends of tubular extensions 46A and 46B are closed off by valve means comprising valve members 48A and 48B and leaf springs 52A and 52B that are formed integral with the valve members. The valve members have round bottom surfaces that are sized and shaped to seat on and close off the upper ends of tubular extensions 46A and 46B. Valve members 48A and 48B and their leaf springs may be molded of a light weight plastic material. The free ends of the leaf springs engage the side walls of blind holes 32A and 32B. The leaf springs function to hold the valve members 48A and 48B in closed position against the upper ends of tubes 46A and 46B, as shown in FIG. 5. However, the leaf springs are relatively weak, having a stiffness just sufficient to hold valve members 46A and 46B in closed position, but low enough to permit the valve members to pivot up off of the tubes to the position shown in FIG. 10B under the influence of air forced up into the tubes, whereby to allow air streams to pass into the orifice insert via its side openings 28A and 28B.

Figure 12:
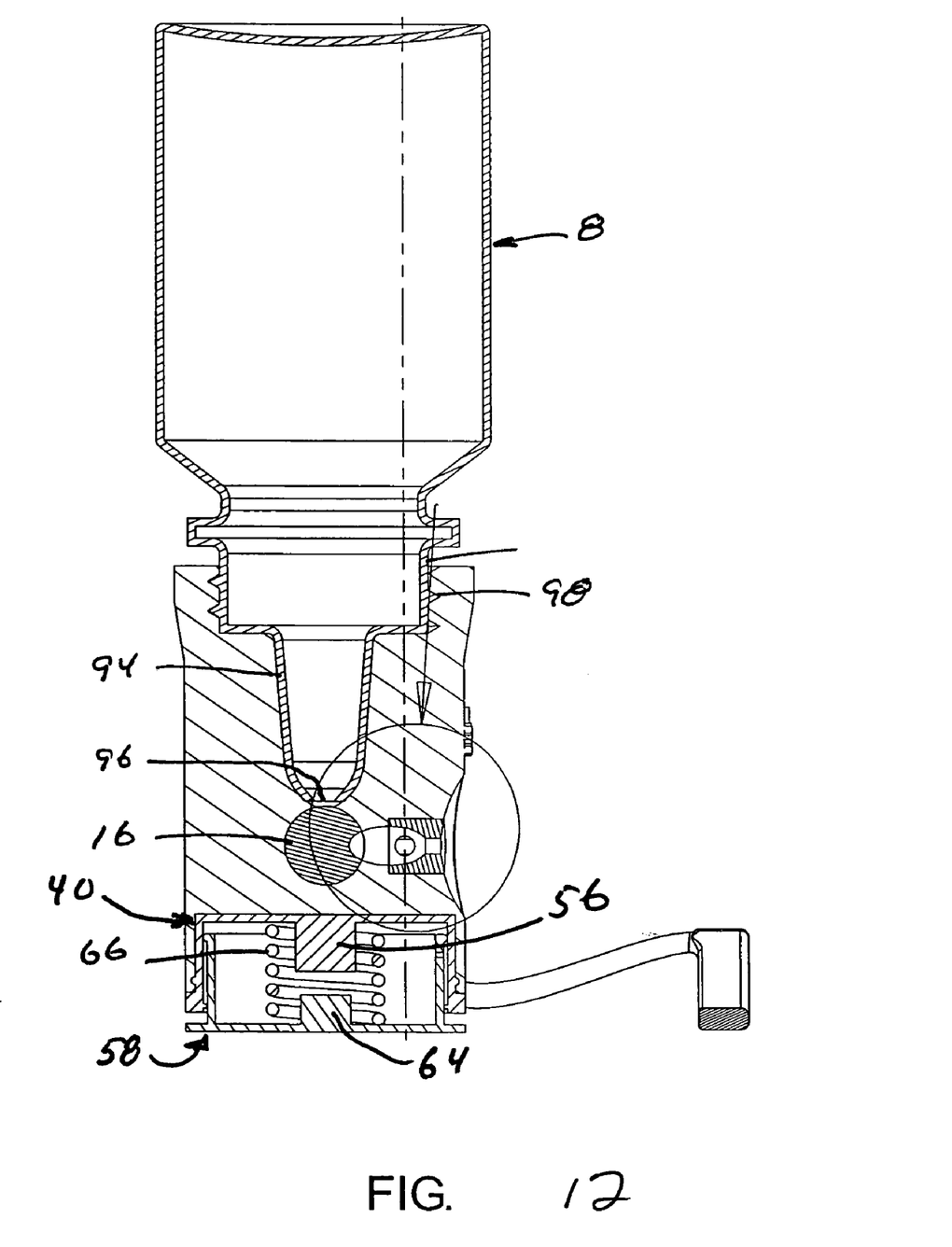
FIG. 12 is a longitudinal sectional view in elevation like FIG. 4 but showing the device with a bottle attached and with the device in discharge position.

Referring to FIGS. 4 and 12, cup shaped member 40 is formed with a center post 56 depending form its end wall 44. Telescopically engaged with and protruding into cup-shaped member 40 is a cup-shaped piston member 58 characterized by a tubular side wall 60 and a bottom wall 62. The latter also has a center post 64 aligned with post 56. A compression spring 66 surrounds posts 56 and 64 and acts to urge piston member 58 outwardly of cup-shaped member 40, i.e., away from cavity 4. The inner end of piston member 58 is provided with a peripheral bead or flange 68 and the cup-shaped member 40 is provided with an internal bead 70 that acts as a stop for bead 68, thereby limiting outward movement of the piston 58. One or more small vent ports 72 (FIG. 4) are formed in side wall 60 of piston member 58 to allow air to bleed into the piston when the latter is in its extended (at-rest) position (FIGS. 1–3, 4 and 5). Ports 72 are located adjacent to the inner ends of piston member 58.

As seen in FIGS. 1–3 and 7, the metering member 16 is provided with square extensions 80 at its opposite ends. These extensions act as keys for making a locking engagement with square holes 82 in two connection members 84A and 84B that are attached to and are movable by a curved lever 86. The flat outer faces of bosses 14 are engaged by and act as bearing surfaces for connection members 84A and 84B as they are rotated by manipulation of lever 86. The latter comprises a pair of arms 88A and 88B that are curved and are attached to a curved cross member 90. Lever 86 is used to rotate metering member 16 from a first position in which the cavity 18 is aligned with the hole 13 at the bottom of cavity 4 and a second position in which the cavity 18 is aligned with radial bore 20 and the center axis of orifice insert 22.

Referring now to FIG. 12, there is shown a bottle 8 of the type used to contain an ophthalmic solution. The bottle has a cylindrical discharge section 92 that is terminated by a tapered nozzle section 94 having a small discharge opening 96 at its tip. Typically the interior diameter of nozzle section 94 varies from about 4 to about 5 mm. nearest the bottle to a diameter of approximately 2 mm. at opening 96. Tubular discharge section 92 is provided with an exterior screw thread 98 for mating with a screw cap (not shown). The screw thread 6 of cavity 4 is designed to mate with screw thread 98, whereby the bottle and the applicator device may be coupled together by a screw connection as shown in FIG. 12. The shape and size of cavity 4 is set so that it will accommodate nozzle section 94 and so that discharge opening 96 will be aligned with and located in proximity to hole 13 and metering member 16 when the bottle and applicator device have been connected as shown.

Preferably, but not necessarily, the body 2 has a tapered depressed surface 33 surrounding the outer end of radial bore 20 and orifice insert 22 is sized so that its outer end is substantially flush with the center (innermost) section of depressed surface 33. Preferably also the outer end of face of insert 22 has a concave shape so as to form a continuation of depressed surface 33, as shown in FIGS. 8 and 9. Recessing the insert 22 in body 2 assists in keeping orifice 24 clean. The depressed surface 33 surrounding the orifice 24 is advantageous for self-medicating uses, since that surface makes it easier to aim the device so as to assure the ophthalmic fluid expelled from orifice 24 is directed at the user's eye.

Operation of the above-described device is straightforward. Assume that the applicator device has been screwed onto a bottle 8 containing an ophthalmic solution as shown in FIG. 12 and that lever 86 is in the raised position shown in FIGS. 1 and 2, so that metering chamber 18 is aligned with cavity 4 (as shown in FIG. 4). If the device is oriented so that the bottle is above it, as shown in FIG. 12, ophthalmic liquid will flow out of the bottle by gravity through hole 13 into cavity 18 in metering member 16. If now lever 86 is pulled down through an angle of 90° (FIG. 12), metering member 16 will be rotated to its second position wherein metering cavity 18 will be aligned with radial bore 20, causing liquid in cavity 18 to fall into and be stored temporarily in a holding chamber that comprises the inner end of bore 20 and the flared counterbore 26 at the inner end of orifice insert 22. At this point, the liquid in the holding chamber will not leak out through the orifice 24 due to the orifice 24 being small enough for surface tension to prevent leakage of the liquid. If thereafter, piston 58 is pushed inwardly, air trapped in the space between cup 40 and piston 58 will be compressed and forced upwardly in tubes 46A and 46B, causing valve members 48A and 48B to pivot to the open position (shown in FIG. 10) and thereby allowing the compressed air to pass from tubular members 46A and 46B to orifice 24 via the side openings 28 in the orifice insert 22. As the air streams pass out of tubular members 46A and 46B into the holding chamber formed by bore 20 and counterbore 26 they merge and have the effect of entraining the ophthalmic liquid in that chamber and expelling it out through the orifice 24, with the entrained liquid being expelled in the form of a spray. Once the liquid has been discharged, piston 58 is released, whereupon spring 66 forces the piston back to its extended position and valve members 48A and 48B drop back to close off tubular extensions 46A and 46B (FIG. 5). The outward (return) movement of the piston has the effect of allowing air to be sucked back into the supply chamber through the small vent ports 72. Metering member 16 may be returned to its standby or fill position (FIG. 2) before or after the piston 58 is operated to expel a dose of liquid. Preferably returning the metering member 16 to its standby or fill position is accomplished before liquid has been expelled from the device. In this connection it is to be noted that when the lever 86 is in the up position (FIG. 2) the metering member 16 may be said to be in the passive or filling position, and when the lever is pulled down 90°, the metering member is said to be in the active or discharge position wherein a predetermined amount of ophthalmic solution is deposited in the holding chamber ready to be air-expelled via the orifice 24. The device is sized so that when the lever 86 is in its second 90° position (FIG. 12) and engaged with the user's face, the orifice 24 will be approximately 1.25 inches from that person's eye, thereby limiting dispersion of the ophthalmic liquid spray to the area of the intended target, i.e., the user's eye.

The invention has a number of advantages. For one thing, it is designed to hold a conventional form of bottle of the type typically used for storing and dispensing ophthalmic medications. All that is required is to remove the cap from the bottle and screw the device onto the mouth of the bottle. A further advantage is that the device is designed to meter a small quantity, preferably approximately 10 μl, of ophthalmic liquid and to transfer that quantity of liquid to the holding chamber by movement of the metering member. A further advantage is that by appropriately selecting the size of orifice 24, a spray of controlled size can be achieved. The valve members 46A and 46B allow air to flow in the proper direction, closing off backflow of any outside air that may enter trough the orifice 24. Another advantage is that the application housing and certain other parts of the device may be molded of plastic or made of metal.

An important advantage is that the lever 86 may be sized in length so that if its curved end portion 90 is engaged with the cheekbone of the user, the orifice 42 will be spaced a selected distance from the eye calculated to confine the sprayed ophthalmic liquid to within the perimeter of the eye cavity.

The invention is susceptible of a number of modifications. For one thing, the illustrated applicator device may be used with a bottle that does not have an elongate spout as shown at 94 that can extend down to the bottom of cavity 4. In such case, the portion of cavity 4 not occupied by a bottle spout section will serve as a supply chamber for ophthalmic fluid discharged from container 8, and the cavity 18 will be filled by ophthalmic liquid from that supply chamber. It is contemplated also that the dispenser device may be formed as a part of the bottle, with the bottle being filled in the course of or subsequent to the manufacture of the combination bottle/dispenser device.

It is obvious also that a different form of one-way valve means may be used to close off tubular extensions 46A and 46B. For example, leaf springs 52A and 52B may be replaced by small compression springs. Still other modifications will be obvious to persons skilled in the art.

What is claimed is:

1. A device for delivering a metered quantity of a liquid ophthalmic product to an eye comprising:

a body having a first cavity and an opening at the outer end of said cavity that is adapted for surrounding engagement with the mouth of a bottle containing a liquid ophthalmic product, a transverse bore in said body communicating with said first cavity, a discharge orifice at one side of said body, a holding chamber connecting said transverse bore and said discharge orifice, and at least one passageway communicating with said holding chamber;

a metering member rotatably disposed in said transverse bore, said metering member comprising a second cavity for holding a predetermined quantity of a liquid ophthalmic product, said metering member being rotatable between a first position wherein said second cavity is open to said first cavity whereby liquid ophthalmic product can flow via gravity from said first cavity into said second cavity and a second position wherein said second cavity is aligned with said holding chamber and liquid ophthalmic product can spill out of said second cavity into said holding chamber; and selectively operable means for injecting air into said holding chamber via said at least one passageway, whereby said air will expel liquid ophthalmic product from said holding chamber to the atmosphere via said orifice.

2. A device according to claim 1 wherein said orifice comprises a separately formed member that is disposed in a side port in said body, said separately formed member having a relatively large opening facing said holding chamber and a relatively small opening facing the atmosphere exterior of said body.

3. A device according to claim 1 wherein said selectively operable means comprises an air pressure chamber within said body and connected to said at least one passageway, normally closed valve means for controlling flow of air from said air pressure chamber to said at least one passageway; and manually operable piston means for forcing air from said air pressure chamber so as to cause said valve means to open and allow said air to flow into said at least one passageway under pressure.

4. A device according to claim 3 wherein said body has at least one opening communicating at one end with said air pressure chamber and at the other end with said at least one passageway, said normally closed valve means comprises a valve member interposed between said at least one opening and said at least one passageway and spring means urging said valve member into a closed position, said spring means having a relatively low stiffness whereby it can be caused to allow said valve member to open under air pressure applied by movement of said manually operable piston means.

5. A device according to claim 4 wherein said air pressure chamber has an open end, and said piston means comprises a piston member slidably mounted in said open end for telescoping movement relative to said body.

6. A device according to claim 5 wherein said piston means includes a spring urging said piston outwardly of said body.

7. A device according to claim 1 further including means for manually rotating said metering member.

8. A device according to claim 7 wherein said last-mentioned means is located outside of said body.

9. A device according to claim 8 wherein said last-mentioned means is a lever, and further wherein when said metering member is in said second position, said lever will extend laterally of said body along a line generally parallel to the center line of said orifice.

10. A device according to claim 9 wherein said lever has an end portion for engaging a person's face and a length such that when said end portion is engaged with a person's face said orifice will be spaced approximately 1.25 inches from the person's eye.

11. A device according to claim 1 wherein said body has an exterior surface with a flared recessed area surrounding said orifice, whereby to facilitate discharge of fluid from said orifice in the form of a spray.

12. A device according to claim 3 wherein said air pressure chamber comprises an opening at one end of said body in line with said cavity, and said manually operable piston means is in the form of a cup having an end wall and a tubular side wall, with said tubular side wall being disposed in telescoping relation with said opening and said end wall being disposed outside of said body and coating with said tubular side wall to close off said air pressure chamber.

13. A device according to claim 12 further including means preventing said cup from separating from said body.

14. A device according to claim 13 further including a compression spring disposed between said cup and said body and urging said cup outwardly of said body.

15. A device according to claim 3 wherein said air pressure chamber is defined in part by a first cup-shaped member inserted into an opening in said body and in part by said piston means, said piston means comprising a second cup-shaped member mounted in telescoping relation with said first cup-shaped member.

16. A device according to claim 1 wherein said orifice has a longitudinal axis and is oriented so that said axis extends normal to the axis of rotation of said metering member.

17. A device according to claim 16 wherein said opening at the outer end of said first cavity is adapted to hold a bottle so that it is normal to the axis of rotation of said metering member and normal to the longitudinal axis of said orifice.

18. A device according to claim 1 wherein said second cavity has a volume of about 10 to about 12 microliters.

19. A device for delivering a metered quantity of a liquid ophthalmic product to an eye comprising:

a body having first and second ends and an interior opening, means at said first end for supporting a bottle containing a liquid ophthalmic product so that the interior of said bottle communicates with said interior opening, a holding chamber in said body displaced 90° from said interior opening, and a discharge orifice communicating with said holding chamber;

rotatable metering means in said body for receiving a small amount of liquid ophthalmic product from said bottle via said interior opening and transferring said small amount of liquid ophthalmic product to said holding chamber;

manually operable means exterior of said body for rotating said metering means between a first position in which it communicates with said interior opening and a second position in which it communicates with said holding chamber; and pneumatic means for expelling said small amount of liquid ophthalmic product from said holding chamber and discharging it via said discharge orifice in the form of a spray.

20. A device according to claim 19 wherein said pneumatic means comprises a passageway connecting with said holding chamber, and manually operable piston means disposed in said body at said second end thereof for forcing a stream of pair through said passageway to said discharge orifice, whereby liquid ophthalmic product in said holding chamber is entrained in said air stream and expelled from said orifice as an atomized spray.

21. A device in accordance with claim 20 further including a bottle containing a liquid ophthalmic product, said bottle having a mouth attached to said body and communicating with said interior opening.

22. A device according to claim 21 wherein said discharge orifice is sized so that the surface tension of said liquid ophthalmic product prevents it from leaking out of said holding chamber via said discharge orifice.

23. A device for delivering a metered quantity of a liquid ophthalmic product to an eye comprising:

a body having a transverse bore, an internal cavity having an inner end with a first opening that communicates with said bore and an outer end with a second opening that is adapted for connection with the mouth of a bottle containing a liquid ophthalmic product, a discharge orifice at one side of said body, a holding chamber connecting said transverse bore and said discharge orifice, and at least one passageway communicating with said holding chamber;

a metering member rotatably disposed in said transverse bore, said metering member comprising a cavity for holding a predetermined quantity of a liquid ophthalmic product, said metering member being rotatable between a first position wherein said cavity communicates with said first opening and liquid ophthalmic product can flow into said cavity via gravity from a bottle that is connected to said second opening and a second position wherein said cavity is aligned with said holding chamber and liquid ophthalmic product can spill out of said cavity into said holding chamber; and selectively operable means for injecting air into said holding chamber via said at least one passageway, whereby said air will expel liquid ophthalmic product from said holding chamber to the atmosphere via said orifice.

24. A device according to claim 23 further including lever means disposed outside of said body and connected to said metering member for manually rotating said metering member from one to the other of said first and second positions.

25. A device according to claim 19 wherein said pneumatic means comprises at least one passageway within said body communicating with said holding chamber, an air pressure chamber in said body connected to said at least one passageway, manually closed valve means for controlling flow of air from said air pressure chamber to said at least one passageway, and manually operable piston means for forcing air from said pressure chamber so as to cause said valve means to open and allow said air to flow into at least one passageway under pressure, whereby liquid ophthalmic product in said holding chamber is entrained in said air and expelled to the atmosphere via said orifice.

* * * * *